United States Patent
Foster et al.

(10) Patent No.: US 10,350,196 B2
(45) Date of Patent: Jul. 16, 2019

(54) LONG-ACTING SPIRO-ISOXAZOLINE FORMULATIONS

(71) Applicant: Zoetis Services LLC, Florham Park, NJ (US)

(72) Inventors: Todd P. Foster, Kalamazoo, MI (US); Laibin Luo, Kalamazoo, MI (US)

(73) Assignee: Zoetis Services LLC, Parsippany, NJ (US)

(*) Notice: Subject to any disclaimer, the term of this patent is extended or adjusted under 35 U.S.C. 154(b) by 0 days.

(21) Appl. No.: 15/024,372

(22) PCT Filed: Sep. 26, 2014

(86) PCT No.: PCT/US2014/057588
§ 371 (c)(1),
(2) Date: Mar. 24, 2016

(87) PCT Pub. No.: WO2015/048371
PCT Pub. Date: Apr. 2, 2015

(65) Prior Publication Data
US 2016/0235720 A1    Aug. 18, 2016

Related U.S. Application Data

(60) Provisional application No. 61/884,467, filed on Sep. 30, 2013.

(51) Int. Cl.
| | | |
|---|---|---|
| *A61K 9/00* | (2006.01) | |
| *A61K 9/16* | (2006.01) | |
| *A61K 47/34* | (2017.01) | |
| *A61K 31/422* | (2006.01) | |

(52) U.S. Cl.
CPC .......... *A61K 31/422* (2013.01); *A61K 9/0019* (2013.01); *A61K 9/1617* (2013.01); *A61K 9/1647* (2013.01); *A61K 47/34* (2013.01)

(58) Field of Classification Search
CPC .... A61K 31/422; A61K 9/0019; A61K 47/34; A61K 9/1617; A61K 9/1647
See application file for complete search history.

(56) References Cited

U.S. PATENT DOCUMENTS

| | | |
|---|---|---|
| 6,136,838 A | 10/2000 | Chern et al. |
| 6,726,918 B1 | 4/2004 | Wong et al. |
| 2005/0118221 A1 | 6/2005 | Blakely et al. |
| 2006/0173060 A1 | 8/2006 | Chang et al. |
| 2012/0232026 A1* | 9/2012 | Curtis ................... A01N 43/90 514/30 |

FOREIGN PATENT DOCUMENTS

| | | |
|---|---|---|
| WO | 2007024719 A2 | 3/2007 |
| WO | 2012/001083 A2 | 1/2012 |
| WO | 2012/120399 A1 | 9/2012 |
| WO | 2013/010238 A1 | 1/2013 |

* cited by examiner

*Primary Examiner* — Snigdha Maewall
(74) *Attorney, Agent, or Firm* — Paul M. Misiak

(57) ABSTRACT

The invention describes a long-acting injectable veterinary composition comprising a spirocyclic isoxazoline, at least one biopolymer, and optionally, at least one veterinary acceptable-carrier, -solvent, -excipient, or any mixture thereof. The invention also includes a method of treating an animal with a parasitic infestation by administering the biopolymeric composition to the animal in need thereof, and a process for preparing the biopolymeric composition.

15 Claims, 1 Drawing Sheet

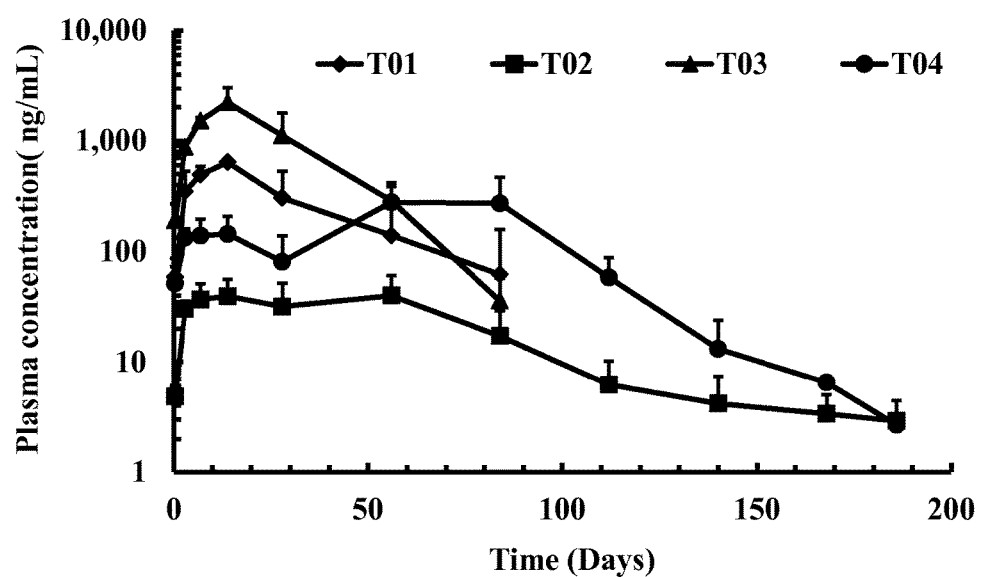
Mean Plasma Concentration Profiles for Compound 1

LONG-ACTING SPIRO-ISOXAZOLINE FORMULATIONS

CROSS-REFERENCE TO RELATED APPLICATIONS

This application is the National Stage of International Application No. PCT/US2014/057588, filed Sep. 26, 2014, which application claims the benefit of U.S. Provisional Application No. 61/884,467, filed Sep. 30, 2013.

FIELD OF INVENTION

This invention relates to a novel long-acting injectable antiparasiticidal composition comprising a spirocyclic isoxazoline and at least one biopolymer, as well as a method of treating an animal with a parasitic infestation with said composition.

BACKGROUND OF THE INVENTION

The present invention relates to a novel long-acting injectable veterinary composition comprising a spirocyclic isoxazoline compound and at least one biopolymer for treating an animal with a parasitic infestation, particularly an ectoparasitic infestation. The biopolymeric composition can be prepared as a solution or suspension for subcutaneous injection. The spirocyclic isoxazolines of the instant invention were originally disclosed in WO2012/120399. The present invention provides an improved long-acting injectable composition for the treatment of a parasitic infestation in an animal. The injectable biopolymeric composition has unique properties including: versatile degradation kinetics, duration of efficacy, and established safety.

Polymeric microparticles have been used for drug delivery for numerous pharmaceutical uses. For example, U.S. Pat. No. 6,726,918 describes a biodegradable implant containing dexamethasone for treating inflammatory ocular conditions; and U.S Patent Application No., 2006-0173060 describes biopolymer microparticles containing an alpha-2-adrenergic receptor agonist for treating glaucoma. Other conditions treated with biopolymer compositions include doxycycline hyclate for periodontal disease, and leuprolide acetate for prostate cancer and endometriosis. Biopolymers have not been described for use in preparing long-acting injectable antiparasitic compositions.

Compositions currently available for parasitic treatment generally include topical, oral, and injectable compositions for animals and do not always demonstrate good activity, good speed of action, or a long duration of action. Most treatments contain hazardous chemicals that can have serious consequences, including lethality from accidental ingestion. Persons applying these agents are generally advised to limit their exposure. Pet collars and tags have been utilized to overcome some problems, but these are susceptible to chewing, ingestion, and subsequent toxicological affects to the animal. Thus, current treatments achieve varying degrees of success which depend partly on toxicity, method of administration, and efficacy. Currently, some agents are actually becoming ineffective due to parasitic resistance. Hence, there is a need for a stable, long-acting, easily administered, and effective long-acting injectable antiparasitic composition.

The veterinary biopolymeric composition of the present invention provides long-acting efficacy in animals against ectoparasites over other known injectable parasiticides.

SUMMARY OF THE INVENTION

The present invention relates to a novel long-acting antiparasitic biopolymeric composition. The composition can be used for the treatment and control of parasitic infestations on animals. Further, the invention contemplates the control and prevention of tick borne diseases, for example, bovine anaplasmosis and babesiosis, Lyme disease, theileriosis, ehrlichiosis, and the like. Thus, according to the present invention, there is provided an improved long-acting biopolymeric composition.

The present invention relates to a long-acting composition comprising a Formula 1 compound

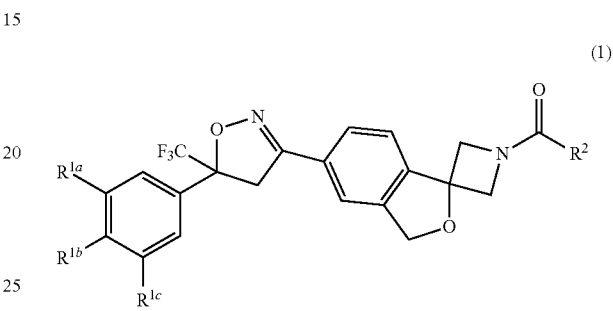

(1)

wherein $R^{1a}$, $R^{1b}$, and $R^{1c}$ are each independently hydrogen, chloro, bromo, fluoro, or trifluoromethyl; and $R^2$ is ethyl, propyl, isopropyl, isobutyl, cyclopropyl, —C(OH)(CH$_3$)$_2$, —CH$_2$cyclopropyl, —CH$_2$CF$_3$, —CH$_2$OH, —CH$_2$SCH$_3$, —CH$_2$S(O)CH$_3$, —CH$_2$S(O)$_2$CH$_3$, —CH$_2$SCF$_3$, 2,2-difluorocyclopropyl, 1,1-dioxidothietane, and —CH$_2$-1H-pyrazole, stereoisomers thereof, and at least one biopolymer. The composition which comprises at least one biopolymer is a biopolymeric composition.

The preferred spirocyclic isoxazoline compound of the present invention is the compound of Formula 1 wherein $R^{1a}$ and $R^{1c}$ are both chloro, $R^{1b}$ is fluoro, and $R^2$ is —CH$_2$S(O)$_2$CH$_3$, and wherein the compound name is 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, or a veterinarily acceptable salt thereof. The more preferred compound is the (S) isomer of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (Compound 1), or a veterinary acceptable salt thereof. The (S)-isomer can be in a crystalline or amorphous solid state form prior to preparing the biopolymeric composition.

In yet another aspect of the invention, the at least one biopolymer is selected from the group consisting of polylactic acid (PLA), poly(glycolic acid) (PGA), polycaprolactone (PCL), poly(lactide-co-glycolide) (PLGA), poly(lactide-co-caprolactone) (PLACL), poly(glycolide-co-caprolactone) (PGACL), glyceryl tristearate (GTS), and any mixture thereof. In yet another aspect of the invention, the at least one biopolymer is selected from the group selected from poly(D,L-lactide-co-glycolide), poly(D,L-lactide), polyglycolide, glyceryl tristearate, and any mixture thereof.

In another aspect of the invention, the biopolymeric composition comprises a spirocyclic isoxazoline, preferably, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, further comprises at least one veterinary acceptable-carrier, -solvent, -excipient, or any mixture thereof.

In another aspect of the invention, the biopolymeric composition comprises a spirocyclic isoxazoline, preferably, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, comprises at least one veterinary acceptable solvent. The particular solvent used can be evaporated to prepare microspheres or can be retained to prepare an injectable depot composition.

In another aspect of the invention, the biopolymeric composition comprising a spirocyclic isoxazoline, preferably, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, further comprises at least one veterinary acceptable carrier.

In another aspect of the invention, the biopolymeric composition comprising a spirocyclic isoxazoline, preferably, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, further comprises at least one veterinary acceptable-carrier and -excipient.

In yet another aspect of the invention, the biopolymeric composition comprises a spirocyclic isoxazoline, preferably, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, at least one veterinary acceptable-solvent and -excipient.

In another aspect of the invention, the biopolymeric composition comprising a spirocyclic isoxazoline, preferably, (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, further comprises at least one veterinary acceptable-carrier and -solvent.

In yet another aspect of the invention, the biopolymeric composition comprises (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone and at least one veterinary acceptable carrier selected from water or triacetin.

In yet another aspect of the invention, the biopolymeric composition comprises (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, water or triacetin, and at least one additional veterinary acceptable-carrier, -solvent, -excipient, or any mixture thereof.

In yet another aspect of the invention, the solvent for preparing the biopolymeric composition is selected from at least one polar solvent or at least one non-polar solvent, or any mixture thereof. Non-limiting examples of polar solvents include: dichloromethane, tetrahydrofuran, ethyl acetate, pyrrolidone(s), acetone, dimethylformamide, acetonitrile, dimethyl sulfoxide, propylene carbonate, ethylene glycol, n-butanol, isopropanol, n-propanol, methylene chloride, ethanol, and methanol. Non-limiting examples of non-polar solvents include: pentane, cyclopentane, hexane, cyclohexane, benzene, toluene, 1,4-dioxane, chloroform, perchloromethane, and diethyl ether.

In yet another aspect of the invention is a process for preparing microspheres for injection by dissolving a spirocyclic isoxazoline of Formula 1 in at least one solvent, adding at least one biopolymer, and optionally, at least one veterinary acceptable excipient, mixing the solution, evaporating off the solvent(s), and collecting the precipitated microspheres that are matrixed with the spirocyclic isoxazoline, and optionally the excipient(s). The microspheres of the instant invention consist of solid hydrophobic fat such as triglycerides or fatty acid derivatives. The microspheres can then be suspended in at least one veterinary acceptable carrier, and optionally, at least one excipient, for injection.

In yet another aspect of the invention is a process for preparing the injectable composition by dissolving a spirocyclic isoxazoline of Formula 1 and at least one biopolymer in at least one veterinary acceptable solvent, and optionally, at least one veterinary acceptable-carrier, -excipient, or mixture thereof, for injection.

In yet another aspect of the invention, the biopolymeric composition comprises at least one veterinary acceptable carrier selected from the group consisting of water, ethanol, 1-propanol, 2-propanol, 1-butanol, 2-butanol, 1-pentanol, 2-pentanol, 3-pentanol, propylene glycol, polyethylene glycols (PEG): PEG 200, PEG 300, and PEG 400; diethylene glycol ethyl ether, isopropylidene glycerol, dimethyl isosorbide, propylene carbonate, glycerol, pyrrolidones (non-limiting examples include: N-methylpyrrolidone, 2-pyrrolidone, N-pyrrolidone, polyvinylpyrrolidone, and the like), methylethylketone (MEK), dimethylsulfoxide (DMSO), 1-dodecylazacyclo-heptane, dipropyleneglycol methyl ether, ethyl lactate, dimethylformamide, N,N-diethyl-m-toluamide, dimethylacetamide, ethylacetamide, caprolactam, decylmethylsulfoxide, triacetin, solketal, propylene carbonate, ethyl lactate, and any mixture thereof.

In yet another aspect of the invention, the veterinary biopolymeric composition is an injectable composition. In another aspect of the invention, the injection is a subcutaneous injection. In another aspect of the invention, the injection is a intramuscular injection. In another aspect of the invention, the biopolymeric composition is a suspension. In yet another aspect of the invention, the biopolymeric composition is a solution.

In yet another aspect of the invention, the long-acting biopolymeric composition is administered at least once every 2-months, 3-months, 4-months, 5-months, 6-months, 7-months, 8-months, 9-months, 10-months, 11-months, or 12-months. In yet another aspect of the invention, the long-acting biopolymeric composition is administered at least once every 3- to 6-months. In yet another aspect of the invention, the long-acting biopolymeric composition is administered at least once every 3-months, 4-months, 5-months, or 6-months. In yet another aspect of the invention, the long-acting biopolymeric composition is administered at least once every 3-months. In yet another aspect of the invention, the long-acting biopolymeric composition is administered at least once every 4-months. In yet another aspect of the invention, the long-acting biopolymeric composition is administered at least once every 5-months. In yet another aspect of the invention, the long-acting biopolymeric composition is administered at least once every 6-months.

In yet another aspect of the invention is a method of treating an animal with a parasitic infestation comprising administering a biopolymeric composition comprising a spirocyclic isoxazoline. In yet another aspect of the invention, the spirocyclic isoxazoline is an effective amount of said spirocyclic isoxazoline. In yet another aspect of the invention, is a method of treating an animal with a parasitic infestation comprising administering a biopolymeric composition comprising an effective amount of (S)-1-(5-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone.

In yet another aspect of the invention, is a method of treating an animal with a parasitic infestation comprising administering a biopolymeric composition comprising an effective amount of (S)-1-(5-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, further comprising at least one veterinary acceptable carrier, and optionally, at least one veterinary acceptable-solvent or -excipient, or mixture thereof.

In yet another aspect of the invention, the animal is a companion animal or livestock. In yet another aspect of the invention, the companion animal is feline, canine, and equine. In yet another aspect of the invention, the companion animal is feline and canine. In yet another aspect of the invention, the companion animal is feline. In yet another aspect of the invention, the companion is canine. In yet another aspect of the invention livestock is ovine, swine, and bovine. In yet another aspect of the invention, livestock is ovine. In yet another aspect of the invention, livestock is bovine. In yet another aspect of the invention, livestock is swine.

In yet another aspect of the invention, the parasite is an ectoparasite. In yet another aspect of the invention, the ectoparasite is an acarine or an insect. In yet another aspect of the invention, the acarine is a tick. In yet another aspect of the invention, the acarine is a mite. In yet another aspect of the invention, the insect is a flea, louse, fly, or mosquito.

DEFINITIONS

For purposes of the present invention, as described and claimed herein, the following terms and phrases are defined as follows:

"About" when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

"Animal" as used herein, unless otherwise indicated, refers to an individual animal, and said individual animal is a mammal. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, llama, and horse. Preferred companion animals are dog, cat, and horse. More preferred is dog or cat. Non-exclusive examples of livestock include: swine, rabbits, goat, sheep, deer, elk, cattle, and bison. Preferred livestock is cattle.

"Biopolymer" as used herein, unless otherwise indicated, refers to a biodegradable, bioerodable, and/or biocompatible polymer. A biocompatible polymer refers to a polymer that when administered to an animal does not induce a significant inflammatory response. A biodegradable polymer is a polymer that degrades in vivo, and wherein erosion of the polymer or polymers over time occurs concurrent with or subsequent to release of the therapeutic agent (i.e., a compound of Formula 1). For example, polymers that degrade at a rate that produces monomeric or oligomeric subunits or other byproducts at non-toxic concentrations in the animal. Specifically, hydrogels such as methylcellulose which act to release drug through polymer swelling are specifically excluded from the term biopolymer. The terms "biodegradable" and "bioerodible" are equivalent and are used interchangeably herein. A biopolymer may be a homopolymer, a copolymer, or a polymer comprising more than two different polymeric units. Biopolymeric composition herein refers to a composition comprising at least one biopolymer.

"Excipient", as used herein, unless otherwise indicated, refers to veterinary acceptable excipients (components) of the biopolymeric composition including, for example, viscosity and isotonic modifiers, binders, pore forming agents, additives, preservatives, antioxidants, dispersants, dyes, and the like.

"Infestation", as used herein, unless otherwise indicated, refers to the state or condition of having parasites on the body. Furthermore, the infestation may lead to an infection on or in the animal, which may be microbial, viral, or fungal.

"Long-acting", as used herein, unless otherwise indicated, refers to the duration of time between dosing. The duration refers to administration of the composition at least once every 2-months, 3-months, 4-months, 5-months, 6-months, 7-months, 8-months, 9-months, 10-months, 11-months, or 12-months, and includes fractional durations within the aforementioned monthly dosing intervals. Administration of the polymeric composition comprising a spirocyclic isoxazoline of the present invention that when introduced into an animal by injection, the polymeric composition releases the active agent over a predetermined time period and at a therapeutic level sufficient to achieve a desired therapeutic effect throughout the predetermined time period. Reference to release (for example, sustained or controlled) is intended to encompass release that occurs as the result of biodegradation in vivo of the microspheres or biopolymer composition, or as the result of metabolic transformation or dissolution of the active agent.

"Microsphere", as used herein, unless otherwise indicated, refers to a solid or semi-solid sphere formed from a biopolymer having a spirocyclic isoxazoline of Formula 1, e.g., Compound 1, dispersed throughout.

"Parasite(s)", as used herein, unless otherwise indicated, refers to ectoparasites. Ectoparasites are organisms of the Arthropoda phylum (arachnids and insects) which feed through or upon the skin of its host. Preferred arachnids are of the order Acarina (acarines), e.g., ticks and mites. Preferred insects are of the Order Diptera which include biting or myiasis-inducing flies (midges, mosquitos, stable fly, horn fly, blow fly (e.g., cochliomyia), horse fly, sand fly, and the like), *Siphonaptera* (fleas), and Phthiraptera (lice). Parasites also encompasses the different life stages of the ectoparasite, including eggs, pupae, and larvae which feed on or in the body.

"Therapeutically effective amount", as used herein, unless otherwise indicated, refers to an amount of one of the spirocyclic fluoro-azetidine isoxazolines of the present invention that (i) treat or prevent the particular parasitic infestation, (ii) attenuates, ameliorates, or eliminates one or more symptoms of the particular parasitic infestation, or (iii) prevents or delays the onset of one or more symptoms of the particular parasitic infestation described herein. A dose range of about 1 to 50 mg/kg is contemplated to be a therapeutically effective dose. Dose volumes include about 1 to about 200 mg/mL, preferred dose volumes range from about 5 to about 150 mg/mL, more preferred dose volumes range from about 10 to 100 mg/mL, more preferred dose volumes range from about 15 to 50 mg/mL.

"Treatment", "treating", and the like, as used herein, unless otherwise indicated, refers to reversing, alleviating, or inhibiting the parasitic infestation. As used herein, these terms also encompass, depending on the condition of the animal preventing the onset of a disorder or condition, or of symptoms associated with a disorder or condition, including reducing the severity of a disorder or condition or symptoms associated therewith prior to affliction with said infestation. Thus, treatment can refer to administration of the composition of the present invention to an animal that is not at the time of administration afflicted with the parasitic infestation, for example, as prophylactic treatment. Treating also encompasses preventing the recurrence of an infestation or of symptoms associated therewith as well as references to "control" (e.g., kill, repel, expel, incapacitate, deter, eliminate, alleviate, minimize, and eradicate).

"Veterinary acceptable" as used herein, unless otherwise indicated, suggests that the substance or composition must be compatible chemically and/or toxicologically with the other ingredients comprising the composition and/or the animal being treated therewith. Veterinary acceptable also encompasses pharmaceutically acceptable.

The phrase, "at least one", as used herein, unless otherwise noted, refers to one or more of a carrier, solvent, excipient, or any mixture thereof.

The phrase "weight %" or "w/w", or "w/w %" as used herein, unless otherwise noted, refers to the weight of one component relative to the total weight of the composition.

BRIEF DESCRIPTION OF THE DRAWINGS

FIG. 1. Mean Plasma Concentration Profiles for Compound 1

DETAILED DESCRIPTION

It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents.

The spirocyclic isoxazoline compounds of the instant invention are characterized according to Formula (1):

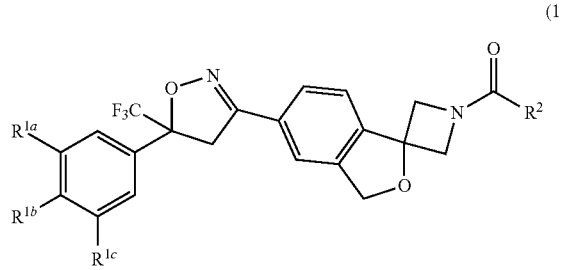

(1)

wherein $R^{1a}$, $R^{1b}$, and $R^{1c}$ are each independently hydrogen, chloro, bromo, fluoro, or trifluoromethyl; and $R^2$ is ethyl, propyl, isopropyl, isobutyl, cyclopropyl, —C(OH)(CH$_3$)$_2$, —CH$_2$cyclopropyl, —CH$_2$CF$_3$, —CH$_2$OH, —CH$_2$SCH$_3$, —CH$_2$S(O)CH$_3$, —CH$_2$S(O)$_2$CH$_3$, —CH$_2$SCF$_3$, 2,2-difluorocyclopropyl, 1,1-dioxidothietane, and —CH$_2$-1H-pyrazole.

The spirocyclic isoxazolines of Formula (1) can be synthesized according to procedures described in WO2012/120399.

It is to be understood that the spirocyclic isoxazoline compounds of the invention contain an asymmetric carbon (chiral) atom, thus compounds of the invention can exist as two or more stereoisomers. Included within the scope of the present invention are all stereoisomers such as enantiomers (e.g. S and R enantiomers) and diasteromers, all geometric isomers and tautomeric forms of the spirocyclic isoxazoline compounds. The spirocyclic isoxazolines of the present invention can be racemates, which include the (S) and (R) enantiomers. Further, the spirocyclic isoxazolines of the present invention can be crystalline or amorphous prior to being dissolved to prepare the biopolymeric composition.

The present invention provides for a composition for the treatment of a parasitic infestation in an animal which comprises a veterinarily effective amount of a spirocyclic isoxazoline compound. The spirocyclic isoxazolines of the present invention include the compounds selected from: 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-((trifluoromethyl)thio)ethanone; (5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone; 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone; 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxyethanone; 2-cyclopropyl-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone; 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(1H-pyrazol-1-yl)ethanone; cyclopropyl(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)methanone; 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; 2-(methylsulfonyl)-1-(5'-(5-(3,4,5-trichlorophenyl)-5-(trifluoromethyl)-4,5-dihydroisoxazol-3-yl)-3'H-spiro[azetidine-3,1'-isobenzofuran]-1-yl)ethanone; 1-(5'-(5-(3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; 1-(5'-(5-(3-chloro-5-(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone; 1-(5'-(5-(3,4-dichloro-5-(trifluoromethyl)phenyl)-5-(trifluoromethyl)-4,5-dihydro-isoxazol-3-yl)-3'H-spiro[azetidine-3,1'-isobenzofuran]-1-yl)-2-(methylsulfonyl)-ethanone; 1-(5'-(5-(4-bromo-3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; 1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)

ethanone; 1-(5'-(5-(3-bromo-5-chlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; 1-(5'-(5-(4-chloro-3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone; 1-(5'-(5-(3-chloro-5-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; 1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; and 2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone, including the stereoisomers, veterinary acceptable salts, and the crystalline and amorphous forms thereof.

The preferred spirocyclic isoxazoline is 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (i.e., Formula 1, wherein $R^{1a}$ and $R^{1c}$ are each chloro, $R^{1b}$ is fluoro, and $R^2$ is —$CH_2S(O)_2CH_3$, and stereoisomers thereof. The more preferred compound is the (S) enantiomer of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, which is also referred to herein as Compound 1.

Veterinary compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

In the present invention, the composition is an injectable composition and comprises at least one biopolymer. The injectable composition can be a solution composition (depot) or suspension composition (microsphere). Biopolymers can be either a biodegradable (or bioerodable) polymer or a biocompatible polymer, or a mixture thereof. "Polymer" or "polymeric", or "biopolymer", as used herein, refers to oligomers, adducts, homopolymers, random copolymers, pseudo-copolymers, statistical copolymers, alternating copolymers, periodic copolymer, bipolymers, terpolymers, quaterpolymers, other forms of copolymers, substituted derivatives thereof, and combinations of two or more thereof (i.e., polymer blends). The polymers can be linear, branched, block, graft, monodisperse, polydisperse, regular, irregular, tactic, isotactic, syndiotactic, stereoregular, atactic, stereoblock, single-strand, double-strand, star, comb, dendritic, and/or ionomeric. Combinations of biopolymers can be used as long as they are biocompatible. Non-limiting examples of polymers (biopolymers) include: polylactide, polyglycolide, and poly(lactid-co-glycolide) copolymers. Further, non-limiting examples of polymers include: poly(D,L-lactide-co-glycolide) (PLGA), poly(D,L-lactide) (PLA), polyglycolide (PGA), polycaprolactone (PCL), poly(D, L-lactide-co-caprolactone)(PLACL), poly(glycolide-co-caprolactone) (PGACL), poly(D,L-lactide-co-glycolide-co-caprolactone) (PLGACL), glyceryl tristearate (GTS), polyethylene glycol (PEG), polydioxanone (PDO), poly(hydroxyl alkanoate) (PHA), poly(vinyl alcohol) (PVA), or other polyesters (e.g., poly(orthoesters), poly(aminoesters), poly(anhydrides), poly(D,L-lactide-caprolactone), poly(organophosphazenes)), or any combination thereof.

Further, polymers include: polyester, polyether, polyanhydrides, polyamides, polycarbonates, polyalkylenes, polyalkylene glycols, polyalkylene oxides, polyalkylene terephthalates, polyvinyl ethers, polyvinyl esters, polyvinyl halides, polyorthoesters, poly(ethylene imines), polyvinylpyrrolidone, poly(esteramides), polyglycolides, polysiloxanes, polyurethanes and copolymers thereof, polyimines, poly capro-, butyro, palero-lactones, polysulphones, polydioxanones, polyacetals, polyketals, polycarbonates, polyphosphoesters, polybutylene, polyterephthalate, polyorthocarbonates, polyphosphazenes, polyurethanes, polytetrafluorethylenes (PTFE), polysuccinates, poly(malic acid), poly(amino acids), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexy-lmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate), polyvinyl chloride, polystyrene, polyvinylpryrrolidone, chitosan, polyhydroxycellulose, polysaccharides, chitin, hyaluronic acid, and copolymers, terpolymers and mixtures thereof. The polymers may be combined to prepare a polymeric composition that renders specific controlled release characteristics for the active agent when administered to an animal as long as the mixture is biocompatible.

The polymers polylactic acid, polyglycolic acid, and polylactic-glycolic acid copolymer (PLGA), have been investigated extensively. These polymers are polyesters that, upon administration to an animal, undergo simple hydrolysis. The products of such hydrolysis are biologically compatible and metabolizable moieties (e.g., lactic acid and glycolic acid), which are eventually removed from the body by the citric acid cycle. Polymer biodegradation products are formed at a very slow rate, and hence do not affect normal cell function. To minimize the toxicity of the intact polymer carrier and its degradation products, polymers have been designed based on naturally occurring metabolites.

The release of the spirocyclic isoxazoline (active agent) from these polymeric systems can occur by two different mechanisms. The active agent can be released by diffusion through aqueous filled channels generated in the dosage form by the dissolution of the active agent or by voids created by the removal of the polymer solvent during the original microencapsulation. The second mechanism is enhanced release due to the degradation of the polymer. With time the polymer begins to erode and generates increased porosity and microstructure within the device. This creates additional pathways for drug release. The degradation of the polymers occurs by spontaneous hydrolysis of the ester linkages on the backbone. Thus, the rate can be controlled by changing polymer properties influencing water uptake. These include the monomer ratio (lactide to glycolide), the use of L-lactide as opposed to D/L lactide, and the polymer molecular weight. These factors determine the hydrophilicity and crystallinity which ultimately govern the rate of water penetration. Hydrophilic components such as salts, carbohydrates and surfactants can also be incorporated to increase water penetration into the devices and thus accelerate the erosion of the polymer, these hydrophilic components are also construed as excipients. By altering the properties of the polymer and the properties of the dosage form, one can control the contribution of each of these release mechanisms and alter the release rate of active agent. Slowly eroding polymers such as poly L-lactide or high molecular weight poly(lactide-co-glycolide) with low glycolide compositions will cause the release to become diffusion controlled. Increasing the glycolide composition and decreasing the molecular weight enhances both water uptake and the hydrolysis of the polymer and adds an erosion component to the release kinetics. The release rate can also be controlled by varying the loading of active agent within the microspheres. Increasing the loading will increase the network of interconnecting channels formed upon the dissolution of the active agent and enhance the release of drug from the microspheres. The preferred range of active agent loadings is in the range of about 2 to 50% (w/w). Polymer hydrolysis is accelerated at acidic or basic pH's and thus the inclusion of acidic or basic additives (excipients) can be used to modulate the polymer erosion rate. The excipients can be added as particulates, can be mixed with the incorporated active agent or can be dissolved within the polymer or in solution, and are herein considered to be veterinary acceptable excipients.

As described above, release of the active agent from the polymer can be controlled, in part, by the composition of the polymeric composition. Various factors such as the mechanical strength, swelling behavior, capacity to undergo hydrolysis all can affect release rates of the drug-release material, as is known in the art. The polymer can be engineered and specifically designed and/or selected to provide the polymeric composition with the desired biodegradation rate and release profile of the active agent for a selected duration. The release profile can be manipulated such as by adjusting features of the composition like polymer(s), changing the ratio of components of the polymeric material, ratio of the monomers in the co-polymers, and level of active agent loading. The ratio of polymer to active agent can vary as well. For example, the polymer to active agent ratio can include 1:2, 1:4, 1:8, 1:16, 1:32, 1:64, 1:128, 1:256, 1:512, or any other desirable ratio, for example 2:1, 3:1, 4:1, thereby releasing the active agent over a certain period of time ranging from hours, to days, to weeks, and to months.

Equally important to controlling the biodegradation of the polymer and hence the extended release profile of the implant (microsphere complex) is the relative average molecular weight of the polymer employed in the implant. Different molecular weights of the same or different polymers may be included in the implant to modulate the release profile. In certain implants, the relative average molecular weight of the polymer will range from about 5 to about 100 kD. In certain implants, each biodegradable polymer can have an inherent viscosity from about 0.10 dL/g to about 10 dL/g.

In one aspect of the invention, the microspheres are formed from polylactide-co-glycolide; in another aspect, the microspheres are formed from a blend of PLGA and PLA. Relatively hydrophilic, and preferably carboxylated, polymeric materials such as PLGA are used for a active agent such as Compound 1, which is relatively water soluble, to increase drug loading. Higher molecular weight biopolymers, having different ratios of lactide (which has a longer degradation time, up to one to two years) to glycolide (which has a short degradation time, as short as a few days to a week), are used to provide release over a longer period of time. The combination of drug loading and release rate, as well as the minimization of initial burst release, result in prolonged release of a higher amount of active agent.

In one aspect of the invention, there is a veterinary composition comprising: Compound 1, wherein Compound 1 comprises from about 1 to about 30 w/w % of the composition, and at least one biopolymer. In another aspect of the invention, the veterinary composition comprises a therapeutically effective amount of Compound 1 from about 5 to about 30 w/w % or about 10 to about 30 w/w % or about 15 to about 25 w/w % of the composition. In another aspect of the invention, the veterinary composition comprises a therapeutically effective amount of Compound 1 at about 15 w/w % of the composition. In another aspect of the invention, the veterinary composition comprises a therapeutically effective amount of Compound 1 at about 20 w/w % of the composition. In another aspect of the invention, the veterinary composition comprises a therapeutically effective amount of Compound 1 at about 25 w/w % of the composition. For some aspects of the invention, the biopolymer make up is from 50:50 PLGA to 100% PLA and the molecular weight range is 0.45 to 0.8 dL/g. In another aspect of the invention, the at least one biopolymer comprises poly(lactic-co-glycolic acid) (PLA) or poly(orthoester) (POE) or a combination thereof. The poly(lactic-co-glycolic acid) may comprise a mixture of polyglycolide (PGA) and polylactide and in some embodiments, in the mixture, there is more polylactide than polyglycolide. In various other embodiments in which the polymer or one of the polymers is poly(lactic-co-glycolic acid), there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide. In some embodiments, the biodegradable polymer comprises at least 50 weight % of the formulation, at least 60 weight % of the formulation, at least 70 weight % of the formulation, at least 80 weight % of the formulation, at least 85 weight % of the formulation, at least 90 weight % of the formulation, at least 95 weight % of the formulation or at least 97 weight % of the formulation. In some embodiments, the at least one biopolymer and Compound 1 are the only components of the injectable composition.

The biopolymers can be used to formulate either a microsphere composition (e.g., suspension) or a direct injectable composition (depot composition (e.g., solution)). A depot composition is one that can be injected into a desired location in an animal's body to form an implant, which provides for controlled, sustained release of the active agent. More particularly, the present invention pertains to depot compositions comprising a Formula (1) compound, at least one biopolymer, and at least one veterinary acceptable carrier, and optionally, at least one veterinary acceptable-solvent, -excipient, or mixture thereof. Once injected into an animal, the depot compositional components, e.g., carrier(s), solvents, and excipients, or mixture thereof, diffuse through the tissue while the active agent, which matrices with the biopolymer is retained in the locally deposited injection site which slowly degrades over time thereby releasing the active agent.

Microsphere (including, microparticles and microcapsules) compositions are compositions wherein the biopolymer encapsulates the active agent particles and are solid or semi-solid particles having a diameter of less than one millimeter, and may be less than 100 microns. Microspheres have been used in many different applications, primarily separations, diagnostics, and drug delivery. A number of different techniques can be used to make microspheres from biopolymers including phase separation, solvent evaporation, and spray drying. Generally the biopolymer(s) form the supporting structure of these microspheres, and the drug (agent) of interest (i.e., a spirocyclic isoxazoline of Formula 1, or Compound 1) is incorporated into the biopolymer structure. The microsphere composition further comprises a veterinary acceptable excipient (additive). The microspheres are subsequently suspended in at least one veterinary acceptable carrier prior to injection. The depot composition and the microsphere composition can further comprise at least one other veterinary acceptable-solvent, -excipient, or mixture thereof.

The microspheres can be prepared by numerous techniques. For example, the microspheres can be prepared by solvent evaporation, phase separation, and spray drying techniques.

Solvent evaporation techniques can be used to form microspheres. These techniques generally involve dissolving the biopolymer in a water immiscible organic solvent which contains either dissolved or dispersed active agent (i.e., a spirocyclic isoxazoline of Formula (1)). The polymer/active agent solution is then added to an agitated continuous phase which is usually aqueous. Emulsifiers (excipient) can be included in the aqueous phase to stabilize the oil-in-water emulsion. An emulsion is formed by adding this suspension or solution to a beaker of vigorously stirring water (often containing a surface active agent, for example, polyethylene glycol or polyvinyl alcohol, to stabilize the emulsion). The organic solvent is evaporated while continuing to stir. Evaporation results in precipitation of the biopolymer, forming microspheres containing the active agent (i.e., a compound of Formula 1). Solvent(s) can be removed from the microspheres in a single step, under reduced pressure as described in U.S. Pat. No. 3,691,090; or by application of heat, as described in U.S. Pat. No. 3,891,570. A two-step technique is described in U.S. Pat. No. 4,389,330. Freeze drying has also been used to remove the solvent from microspheres, as reported by Sato, et al, in "Porous Biodegradable Microspheres for Controlled Drug Delivery. Assessment of Processing Conditions and Solvent Removal Techniques," Pharmaceutical Research 5, 21-30 (1988).

Phase separation techniques can also be used to form microspheres. These techniques involve the formation of a water-in-oil emulsion or oil-in-water emulsion. The biopolymer is precipitated from the continuous phase onto the active agent by a change in temperature, pH, ionic strength or the addition of precipitants. For example, U.S. Pat. No. 4,675,800, describes the formation of poly(lactic-co-glycolic) acid microspheres containing active proteins. The protein is first dissolved in the aqueous phase of a water-in-oil emulsion or dispersed as a solid in the polymer phase. Polymer is then precipitated around the aqueous droplets or drug particles by addition of a non-solvent for the biopolymer such as silicone oil.

Spray drying techniques can also be employed to prepare the microspheres. For example, at least one biopolymer is mixed with the active agent together in a solvent, the solvent is evaporated by spraying the solution, leaving polymeric droplets containing the active agent. Spray drying is reviewed in detail by K. Masters in "Spray Drying Handbook" (John Wiley k Sons, New York 1984).

Typical solvents are organic solvents, which can be water miscible or water immiscible. Non-limiting examples of organic solvents include: methylene chloride, chloroform, carbon tetrachloride, dicholorethane, ethyl acetate, methyl acetate, acetone, tetrahydrofuran, pyrrolidones (e.g., N-methylpyrrolidone, N-pyrrolidone, polyvinylpyrrolidone, 2-pyrrolidone, and the like), and cyclohexane. Additional solvents include, but are not limited to, glyceryl acetates (i.e., esters of glycerol and include the monoacetylglycerols, diacetylglycerols, and triacetylglycerol), alcohols such as methanol (methyl alcohol), ethanol, (ethyl alcohol), n-propanol, isopropanol, n-butyl alcohol, 2-butanol, isobutyl alcohol, 2-methyl-2-propanol, n-pentyl alcohol, isopentyl alcohol, neopentyl alcohol, cyclopentyl alcohol, n-hexanol, cyclohexanol, n-heptyl alcohol, n-octyl alcohol, n-nonyl alcohol, n-decyl alcohol, allyl alcohol, benzyl alcohol, diphenylmethanol triphenylmethanol, glycerin, phenol, 2-methoxyethanol, 2-ethoxyethanol, 3-ethoxy-1,2-propanediol, di(ethyleneglycol) methyl ether, 1,2-propanediol, 1,3-propanediol, 1,3-butanediol, 2,3-butanediol, 1,4-butanediol, 1,2-pentanediol, 1,3-pentanediol, 1,4-pentanediol, 1,5-pentanediol, 2,3-pentanediol, 2,4-pentanediol, 2,5-pentanediol, 3,4-pentanediol, 3,5-pentanediol, and combinations thereof.

For the long-acting injectable compositions of the instant invention, typical veterinary acceptable carriers include, but are not limited to: water, ethanol, 1-propanol, 2-propanol, 1-butanol, 2-butanol, 1-pentanol, 2-pentanol, 3-pentanol, propylene glycol, polyethylene glycols (PEG): PEG 200, PEG 300, and PEG 400; diethylene glycol ethyl ether, isopropylidene glycerol, dimethyl isosorbide, propylene carbonate, glycerol, methylethylketone (MEK), dimethylsulfoxide (DMSO), 1-dodecylazacyclo-heptane, dipropyleneglycol methyl ether, ethyl lactate, dimethylformamide, N,N-diethyl-m-toluamide, dimethylacetamide, ethylacetamide, caprolactam, decylmethylsulfoxide, triacetin, solketal, propylene carbonate, ethyl lactate, and mixtures thereof.

The injectable compositions can further comprise at least one additional veterinary acceptable excipient. Typical veterinary acceptable excipients include additives, for example, polymers, lipids, and surfactants. Non-limiting examples of polymer additives include, but are not limited to: poly (ethylene glycol), polyvinylpyrrolidone, poly(vinyl alcohol) (PVA), cellulose (methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt), tri-block copolymer of poly(propylene glycol)-poly(ethylene glycol)-poly(propylene glycol). Non-limiting examples of lipid additives include, but are not limited to: triglycerides, diglycerides, and monoglycerides, such as trilaurate, tripalmitate, and tristearate, fatty acids such as decanoic acid, lauric acid, myristic acid, palmitic acid, stearic acid, and the like; and fatty alcohols, such as lauryl alcohol, myristyl alcohol, cetylic alcohol, stearyl alcohol, and the like. Non-limiting examples of surfactant additives include, but are not limited to: sodium cholate, sodium deoxycholate, sodium glycolate, sodium taurocholate, sodium taurodesoxycholate, lecithin and phospholipids, Tween 20, Tween 40, Tween 80, Span 20, Span 40, Span 60, Span 80, and emulsifiers such as gelatin. Additionally, veterinary acceptable excipients also include, but are not limited to: viscosity modifiers (e.g., hydrophilic polymers, cellulose derivatives, alginic acid, polyvinylpyrrolidone, and mixtures thereof); isotonic modifiers (e.g., sodium chloride, calcium chloride, and the like); stabilizers (e.g., carbohydrates, amino acids and fatty acids); surfactants (e.g., Tween™ and Pluronic™); emulsifier(s); degradation enhancers (e.g., inorganic acids such as ammonium sulfate and ammonium chloride; organic acids such as citric acid, benzoic acid, and ascorbic acid; inorganic bases such as sodium carbonate, potassium carbonate, calcium carbonate, zinc carbonate, and zinc hydroxide; and organic bases such as protamine sulfate, spermine, choline, ethanolamine, diethanolamine, and triethanolamine). Veterinary acceptable excipients can also include pore forming agents to add microstructure to the matrices (i.e., water soluble compounds such as inorganic salts and sugars); dispersion media, antioxidants (e.g., ascorbic acid, citric acid, butylated hydroxytoluene (BHT), butylated hydroxyl anisole (BHA), and the like); preservatives (e.g., benzalkonium chloride, chlorobutanol, phenylmercuric acetate, phenylmercuric nitrate, sodium bisulfite, sodium bisulfate, sodium thiosulfate, thimerosal, methylparaben, polyvinyl alcohol, phenylethyl, antibacterial agents, antifungal agents, and the like); absorption delaying agents; binders; dyes; and other veterinary and/or pharmaceutically acceptable excipients, and combinations thereof, as would be known to one of ordinary skill in the art (see, for example, Remington's Pharmaceutical Sciences, 18th Ed. Mack Printing Company, 1990, pp. 1289-1329. Except insofar as any conventional carrier, solvent, excipient, or any mixture thereof, is incompatible with the active ingredient, its use in the veterinary biopolymeric composition is contemplated.

In the present invention, the long-acting microsphere composition comprises a spirocyclic isoxazoline of Formula (1) and at least one biopolymer, and optionally, at least one veterinary acceptable excipient. This composition can be suspended in at least one veterinary acceptable carrier, for example, water, triacetin, or any other carrier. The composition can further comprise at least one veterinary acceptable-solvent.

The injectable compositions should be suitably buffered if necessary and the veterinary acceptable carrier first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be diluted with a volume of isotonic NaCl solution and sterile water prior to injection. Some variation in dosage will necessarily occur depending on the weight of the animal being treated. The person responsible for administration will, in any event, determine the appropriate dose.

The amounts of these spirocyclic isoxazoline compounds are easily determined by a skilled artisan and further depend on the dose amount and dose volume of the final composition. Representative amounts of a veterinary effective amount of a spirocyclic isoxazoline compound ranges from about 1 mg/kg to about 50 mg/kg, with a preferred range of about 3 mg/kg to about 40 mg/kg. An even more preferred dose of a spirocyclic isoxazoline compound is about 4 mg/kg to about 25 mg/kg. An even more preferred dose of a spirocyclic isoxazoline compound is about 5 mg/kg to about 20 mg/kg. Doses of 5 mg/kg, 10 mg/kg, 15 mg/kg, 20 mg/kg, and 25 mg/kg are herein contemplated.

The spirocyclic isoxazoline long-acting injectable biopolymeric compositions of the present invention are useful as parasiticides for the control and treatment of parasitic infestations in an animal. The veterinary biopolymeric compositions of the present invention have utility as a parasiticide, in particular, as an ectoparasitic. The preferred ectoparasites are acarines and insects. The compositions may, in particular, be used in the fields of veterinary medicine, livestock husbandry, and the maintenance of public health: against acarines and insects which are parasitic upon animals, particularly domestic animals. Domestic animals include companion animals and livestock. Non-limiting examples of companion animals includes: horse, cat, dog, and llamas. Non-limiting examples of livestock include cattle, sheep, goats, swine, and rabbits. Some non-limiting examples of acarine parasites include: ticks (e.g., *Ixodes* spp., *Rhipicephalus* spp., *Boophilus* spp., *Amblyomma* spp., *Hyalomma* spp., *Haemaphysalis* spp., *Dermacentor* spp., *Ornithodorus* spp., and the like); and mites (e.g., *Dermanyssus* spp., *Sarcoptes* spp., *Psoroptes* spp., *Eutrombicula* spp., *Chorioptes* spp., *Demodex* spp., and the like). Some non-limiting examples of parasitic insects include: chewing and sucking lice (e.g., *Damalinia* spp., *Linognathus* spp., and the like); fleas (e.g., *Siphonaptera* spp., *Ctenocephalides* spp., and the like); and flies, mosquitos, and midges (e.g., Order Diptera; *Aedes* spp., *Anopheles* spp., *Tabanidae* spp., *Haematobia* spp., *Stomoxys* spp., *Dermatobia* spp., *Simuliidae* spp., *Ceratopogonidae* spp., *Psychodidae* spp., *Cochliomyia* spp., *Muscidae* spp., *Hypoderma* spp., *Gastrophilus* spp., *Simulium* spp., and the like); true bugs (e.g., Order Hemiptera); cockroaches (*Periplaneta* spp, *Blatella* spp) and wasps and ants (*Hymenoptera* spp).

The veterinary biopolymeric compositions of the present invention are of particular value in the control of ectoparasites which are injurious to, or spread or act as vectors of diseases in animals, for example those described herein, and more especially in the control of ticks, mites, lice, fleas, midges and biting, nuisance flies, that may cause, for example, leishmaniasis, demidicosis, Lyme, and borreliosis. They are particularly useful in controlling acarines and insects which feed on the skin or tissue or suck the blood of the animal, for which purpose they may be administered topically.

The spirocyclic isoxazoline compound binds tightly to ligand-gated chloride channels, in particular those gated by the neurotransmitter gamma-aminobutyric acid (GABA), thereby blocking pre- and post-synaptic transfer of chloride ions across cell membranes in insects and acarines when exposed by ingestion or contact. This mechanism of action results in lethal uncontrolled activity of the central nervous system of insects and acarines yielding highly efficacious control against said ectoparasite.

The method of treating an animal with a parasitic infestation comprises the administration of the long-acting biopolymeric composition comprising a therapeutically effective amount of a spirocyclic isoxazoline compound. Administration is contemplated as an injectable composition. In particular, injectable administration is considered to be subcutaneous injection. The composition can be administered to the animal in need thereof, by administering an effective amount of the biopolymeric composition thereof to the animal at least once every 2-months, 3-months, 4-months, 5-months, 6-months, 7-months, 8-months, 9-months, 10-months, 11-months, or 12-months. The preferred dosing administration is contemplated to be at least once every 4 to 8 months, and more preferrably at least once every 3 to 6 months. Fractional dosing intervals between 2- and 12-months is also contemplated.

The veterinary biopolymeric compositions of the present invention also have value for the treatment and control of the various lifecycle stages of arachnids and insects, including egg, nymph, larvae, juvenile and adult stages.

Moreover, for animal administration, it will be understood that preparations should meet sterility, pyrogenicity, general safety and purity standards as required by local regulatory agencies.

The present invention also relates to a method of administering a veterinary biopolymeric composition of the present invention to an animal in good health comprising the application to said animal to reduce or eliminate the potential for both animal and human parasitic infestation carried by the animal and to improve the environment in which the animals and humans inhabit.

EXAMPLES

Microsphere Composition 1: Glyceryl tristearate (GTS) was mixed with Compound 1 in ethyl acetate. A solution was formed at 80° C. Polyvinyl alcohol (PVA) was heated to 90° C. and then the ethyl acetate solution was added to the heated PVA while stirring. The resulting suspension was stirred for an additional 30 minutes. The solution was then cooled and resulting particles collected by filtration. The product was dried under vacuum at room temperature. The composition can be diluted with water, or other veterinary acceptable carrier, for injection as a suspension. Targeted drug loading (w/w %) was 9.1. Actual drug load (9.1%) was confirmed by HPLC.

Microsphere Composition 2. Poly(D,L-lactide) (PLA) and Compound 1 were dissolved in methylene chloride. The resulting solution was added to 0.5% PVA while stirring. Solids were collected by filtration and dried under vacuum at room temperature. The composition can be diluted with water, or other veterinary acceptable carrier, for injection as a suspension. Targeted drug loading w/w % was 20. Actual drug load (20.7) was confirmed by HPLC.

Microsphere Composition 3. 50:50 Poly(D,L-lactide-co-glycolide) (PLGA), Compound 1, and polyethylene glycol [50:40:10 w/w %] were dissolved in methylene chloride. The resulting solution was used to prepare polymeric microspheres. The solid microsphere composition can be diluted with water, or other veterinary acceptable carrier, for injection as a suspension.

Microsphere Composition 4. 50:50 Poly(D,L-lactide-co-glycolide) (PLGA), Compound 1, and glyceryl tristearate [50:40:10 w/w %] were dissolved in methylene chloride. The resulting solution was used to prepare polymeric microspheres. The solid microsphere composition can be diluted with water, or other veterinary acceptable carrier, for injection as a suspension.

Depot Composition 1. 2-pyrrolidone was mixed with 75:25 PLGA. Triacetin was added to the mixture and then the mixture was heated to 60° C. until the biopolymer dissolved. Compound 1 was added and the mixture sonicated until all solids dissolved. The composition can be injected as a solution, thereby creating a depot-like composition, i.e., one that slowly dissipates from the subcutaneous region following injection.

Depot Composition 2. poly(DL-lactide) (PLA, 1 g)) was mixed with 2-pyrrolidone (about 6 mL) and triacetin (about 8 mL). The mixture was sonicated under heating to prepare a solution. Compound 1 was dissolved into the solution and additional triacetin (qs 20 mL) was added. The composition can be injected as a solution, thereby creating a depot-like composition, i.e., one that slowly dissipates from the subcutaneous region following injection.

Depot Composition 3. poly(DL-lactide) (PLA, 1 g) was mixed with polyethylene glycol (about 100 mg), 2-pyrrolidone (about 6 mL), and triacetin (about 8 mL). The mixture was sonicated under heating to prepare a solution. Compound 1 was dissolved in the solution and additional triacetin (qs 20 mL) was added. The composition can be injected as a solution, thereby creating a depot-like composition, i.e., one that slowly dissipates from the subcutaneous region following injection.

For depot compositions 2 and 3, different viscosities of PLA can be used. These viscosities can range from about 0.29 dL/g to about 0.67 dL/g, all of which are commercially available. Final concentration of Compound 1 was about 20 mg/mL.

BIOLOGICAL

A pharmacokinetic study was conducted in beagle dogs using Compound 1. Compound 1 was administered by subcutaneous injection at a dose range of 5 and 20 mg/kg. Target dose range was 20 mg/mL with a target dose volume of 0.25 mL/kg. Animals were placed in 1 of 6 treatment groups: T01 (Compound 1 (20 mg/mL; 5 mg/kg), glyceryl tristearate, and HPMC, in suspension); T02 (Compound 1 (20 mg/mL; 5 mg/kg), poly(DL-lactide), and HPMC in suspension); T03 (Compound 1 (20 mg/mL; 20 mg/kg) in HPMC, in suspension); and T04 (Compound 1 (20 mg/mL; 5 mg/kg), poly(lactic-co-glycolic acid (PLGA), 2-pyrrolidinone, and triacetin, in solution. Suspension doses are microsphere compositions and the solution is a depot composition. Doses were administered into the intrascapular region. Blood samples (plasma) were obtained predose, 8, 72 (3-days), 168 (7-days), 336 (14-days), 672 (28-days), 1344 (56-days), and 2016 (84-days) hours postdose for all groups. For Groups T02 and T04, additional samples were obtained at 2688 (112-days), 3360 (140-days), 4032 (168-days), and 4464 (186-days). The mean plasma Compound 1 concentrations (ng/mL) for each study group are shown in Table 1 and the mean pharmacokinetic values are shown in Table 2. The mean plasma concentration profiles for the groups are shown in FIG. 1.

TABLE 1

Mean Plasma Concentrations for Compound 1

| Time (hrs) | Time (days) | T01 | T02 | T03 | T04 |
|---|---|---|---|---|---|
| 0 | 0 | blq | blq | blq | blq |
| 8 | 0.33 | 58.4 | 4.81 | 190 | 51.1 |
| 72 | 3 | 346 | 30.1 | 877 | 133 |
| 168 | 7 | 491 | 36.6 | 1510 | 138 |
| 336 | 14 | 638 | 39.2 | 2210 | 143 |
| 672 | 28 | 304 | 31.6 | 1110 | 80.3 |
| 1344 | 56 | 139 | 39.8 | 285 | 277 |
| 2016 | 84 | 61.8 | 17.1 | 35.6 | 271 |
| 2688 | 112 | ns | 6.18 | ns | 57.9 |
| 3360 | 140 | ns | 4.17 | ns | 13.1 |
| 4032 | 168 | ns | 3.36 | ns | 6.47 |
| 4464 | 186 | ns | 2.9 | ns | 2.67 | ns—no sample procured

TABLE 2

| Mean Pharmacokinetic Parameters for Compound 1 | | | | |
| --- | --- | --- | --- | --- |
| | T01 | T02 | T03 | T04 |
| tmax (hr) | 336 | 584 | 336 | 1790 |
| tmax (days) | 14 | 24.3 | 14 | 74.6 |
| Cmax (ng/mL) | 638 | 44.9 | 2210 | 368 |
| t½ (hr) | 451 | nc | 270 | 339 |
| t½ (days) | 18.8 | nc | 11.3 | 14.1 |
| AUC (0-84 days) (µg · hr/mL | 522 | | 1600 | |
| AUC (0-186 days) (µg · hr/mL | na | 80.9 | na | 525 | nc—not calculated
na—not applicable

We claim:

1. A long-acting veterinary injectable microsphere composition wherein the microsphere comprises:
    a) a 38% to 63% drug load consisting of (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
    b) and a poly(D,L-lactide-co-glycolide) biopolymer that is 50% polylactide and 50% polyglycolide or 75% polylactide and 25% polyglycolide or a poly(D,L-lactide); and
    c) at least one veterinary acceptable-carrier selected from water or triacetin; and optionally, at least one veterinary acceptable excipient, and wherein long-acting is at least 3 to 6 months.

2. The composition of claim 1 wherein the veterinary acceptable carrier is water.

3. The composition of claim 2 wherein the (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone is about 20 mg/mL.

4. The composition of claim 1 wherein the composition further comprises at least one veterinary acceptable excipient.

5. The composition of claim 1, wherein the injectable composition is a subcutaneous injectable composition.

6. The long-acting injectable veterinary microsphere composition of claim 1, comprising a poly(D,L-lactide-co-glycolide).

7. The composition of claim 6 wherein the veterinary acceptable carrier is water.

8. The composition of claim 7, wherein the composition is administered by subcutaneous injection.

9. A method of treating an animal with a parasitic infestation comprising administering a long-acting veterinary injectable microsphere composition wherein the microsphere comprises:
    a) a 38% to about 63% drug load consisting of (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
    b) and a poly(D,L-lactide-co-glycolide) biopolymer that is 50% polylactide and 50% polyglycolide or 75% polylactide and 25% polyglycolide or a poly(D,L-lactide);
    c) at least one veterinary acceptable carrier selected from water or triacetin; and
    d) optionally, at least one veterinary acceptable excipient.

10. The method of claim 9 wherein the veterinary acceptable carrier is water.

11. The method of claim 9 or 10 wherein said animal is a companion animal and the composition is administered by subcutaneous injection.

12. The composition of claim 6 wherein the poly(D,L-lactide-co-glycolide) is 75% polylactide and 25% polyglycolide and the veterinary acceptable carrier is water.

13. The composition of claim 12 wherein the biopolymer is poly(D,L-lactide) and the veterinary acceptable carrier is water.

14. The method of claim 9 wherein the biopolymer is a poly(D,L-lactide-co-glycolide) and the veterinary acceptable carrier is water.

15. The method of claim 14 wherein the composition further comprises a veterinary acceptable excipient.

* * * * *